US010604546B2

(12) United States Patent
Holappa et al.

(10) Patent No.: US 10,604,546 B2
(45) Date of Patent: Mar. 31, 2020

(54) METHOD FOR REDUCING COLOUR OF A BIOTECHNOLOGICAL LIQUID

(71) Applicant: Kemira Oyj, Helsinki (FI)

(72) Inventors: Susanna Holappa, Helsinki (FI); Michael Recktenwald, Espoo (FI)

(73) Assignee: Kemira Oyj, Helsinki (FI)

( * ) Notice: Subject to any disclaimer, the term of this patent is extended or adjusted under 35 U.S.C. 154(b) by 541 days.

(21) Appl. No.: 15/037,683

(22) PCT Filed: Nov. 5, 2014

(86) PCT No.: PCT/FI2014/050831
§ 371 (c)(1),
(2) Date: May 19, 2016

(87) PCT Pub. No.: WO2015/075302
PCT Pub. Date: May 28, 2015

(65) Prior Publication Data
US 2016/0289266 A1    Oct. 6, 2016

(30) Foreign Application Priority Data

Nov. 19, 2013  (FI) ..................... 20136148

(51) Int. Cl.
*C07K 1/30* (2006.01)
*C07K 1/14* (2006.01)
*C12N 9/96* (2006.01)

(52) U.S. Cl.
CPC .................. *C07K 1/30* (2013.01); *C07K 1/14* (2013.01); *C12N 9/96* (2013.01)

(58) Field of Classification Search
None
See application file for complete search history.

(56) References Cited

U.S. PATENT DOCUMENTS 5,395,536 A * 3/1995 Brown ...................... C02F 1/26
                                                    210/727

FOREIGN PATENT DOCUMENTS

| CN | 102249894 A   | 11/2011 |
| CN | 102286080 A   | 12/2011 |
| CN | 103100260 A   | 5/2013  |
| EP | 2236630 A1    | 10/2010 |
| FI | 102620 B1     | 1/1999  |
| WO | 9013632 A1    | 11/1990 |
| WO | 9638469 A1    | 12/1996 |
| WO | 2012129652 A1 | 10/2012 |

OTHER PUBLICATIONS

Migo et al. "Decolorization of molasses wastewater using an inorganic flocculant" Journal of Fermentation and Bioengineering vol. 75, Issue 6, 1993, pp. 438-442 (Year: 1993).*
Peter Gebbie "Using Polyaluminium Coagulants in Water Treatment" 64th Annual Water Industry Engineers and Operators' Conference, All Seasons International Hotel—Bendigo Sep. 5 and 6, 2001, 9 pgs (Year: 2001).*
Lessner et al. "Methanogenesis Biochemistry" Encyclopedia of Life Sciences, 2009, 11 pgs (Year: 2011).*
Faria-Oliveria et al. "Yeast: World's Finest Chef" n book: Food Industry, Chapter: 23, Publisher: Intechweb, Editors: Innocenzo Muzzalupo, pp. 519-547, Jan. 2013 (Year: 2013).*
Spectrum "Pore Size Chart" 1995, 1pg (Year: 1995).*
Nelson et al. "An Investigation of Cane-Molasses Distillery Slop with Special Reference to Certain Organic Acids" Ind. Eng. Chem., 1929, 21 (9), pp. 857-859 (Year: 1929).*
Dwyer et al. "Simultaneous colour and DON removal from sewage treatment plant effluent: Alum coagulation of melanoidin" water research 43 ( 2009) 553-561 (Year: 2009).*
Zhou et al. "Decolorization and COD removal of secondary yeast wastewater effluents by coagulation using aluminum sulfate" Desalination 225 (2008) 301-311 (Year: 2008).*
Silva S et al, Downstream processing for xylitol recovery from fermented sugar cane bagasse hydrolysate using aluminium polychloride. Zeitschrift fuer Naturforschung, C: Journal of Biosciences 2000, vol. 55 p. 10-15. abstract CAPLUS online; retrieved Jun. 25, 2014; STN International Accession No. 2000:162091.
Finnish Patent and Registration Office, Search report of Finnish Patent Application No. 20136148, dated Jul. 4, 2016.
Smith R et al, The purification and properties of a fibrinolytic neutral metalloendopeptidase from *Streptococcus faecalis*, Archives of Biochemistry and Biophysics, Academic Press, US, vol. 202, No. 2, Jul. 1, 1980, pp. 629-638.
Rich Joseph O et al, Laccases from Aureobasidium pullulans, Ensyme and microbial technology, Stoneham, MA, US, vol. 53, No. 1, Mar. 28, 2013, pp. 33-37.
Werries E et al, Degradation of biogene oligosaccharides by beta-N-acetylglucosaminidase secreted by Entamoeba histolytica, Molecular and Biochemical parasitology, Elsevier Science Publishers, Amsterdam, NL, vol. 7, No. 2, Feb. 1, 1983, pp. 127-140.
Gao B et al., Characterization and coagulation of a polyaluminum chloride (PAC) coagulant with high A113 content, Journal of Enviromental Engineering, Academic Press, London, GB, vol. 76, No. 2, Jul. 1, 2005, pp. 143-147.
Li F et al.k Preparation and performance of a high purity polyaluminun chloride, Chemical engineering journal, Elsevier Sequoia, Lausanne, CH, vol. 156, No. 1, Jan. 1, 2010, pp. 64-69.

(Continued)

*Primary Examiner* — Thane Underdahl
(74) *Attorney, Agent, or Firm* — Berggren LLP

(57) ABSTRACT

The invention relates to a method for reducing colour of a biotechnological liquid. In the method a biotechnological liquid comprising colour forming substances is obtained and a high-basicity aluminium compound, which has a basicity of at least 0%, is added and mixed to the biotechnological liquid. Precipitate and/or flocks comprising colour forming substances are allowed to form, and the precipitate and/or flocks are separated from the biotechnological liquid.

8 Claims, 1 Drawing Sheet

(56) References Cited

OTHER PUBLICATIONS

Wang Sen et al., Impact of polymer flocculants on coagulation-microfiltration of surface water, Water research, vol. 47, No. 13, May 10, 2013, pp. 4538-4546.
Chinese Patent Office, Office Action and Search Report of the Chinese patent application No. 2014800631806, dated Feb. 22, 2019, 7 pages.
Chen Taosheng: Chemical Industry Press; National Spark Program Series Production Technology of Enzyme Preparation, Jan. 1994.
Wang Yan et al.: Environmental Chemistry, vol. 23, No. 3, May 2004, Preliminary Study on Decolorization Properties of Polyaluminum Chloride Composite Flocculants.

\* cited by examiner

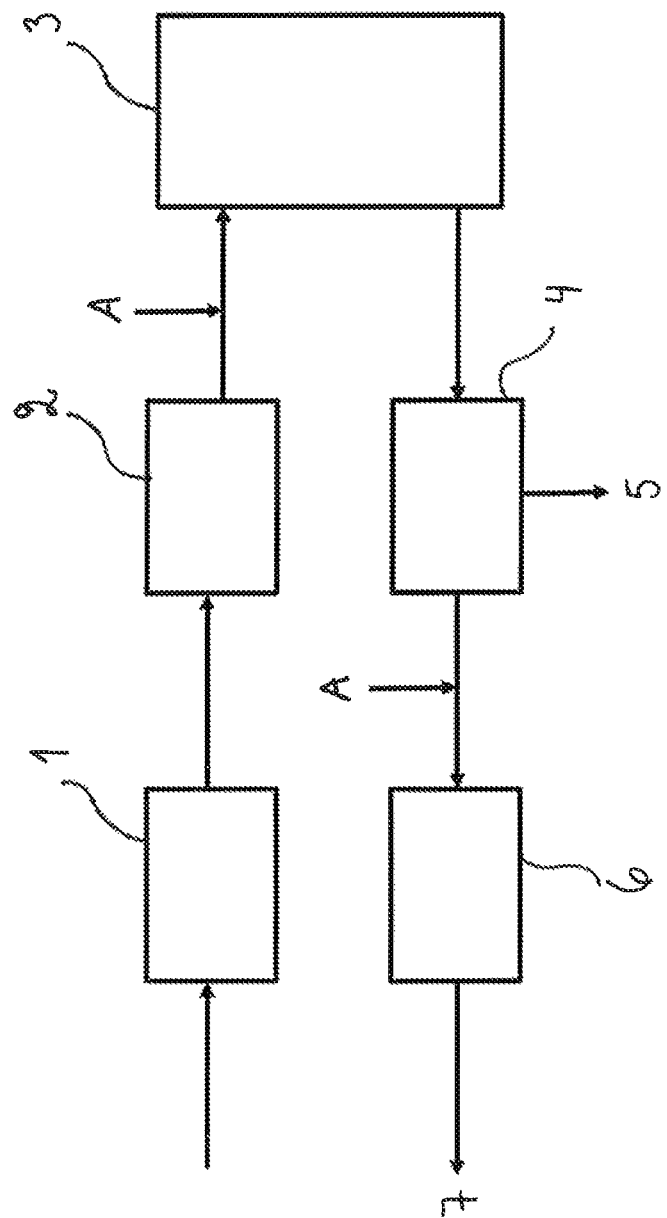

METHOD FOR REDUCING COLOUR OF A BIOTECHNOLOGICAL LIQUID

PRIORITY

This application is a U.S national application of the international application number PCT/FI2014/050831 filed on Nov. 5, 2014 and claiming priority of Finnish national application FI20136148 filed on Nov. 19, 2013, the contents of all of which are incorporated herein by reference.

The present invention relates to a method for reducing colour of a biotechnological liquid according to the preambles of the enclosed claims.

Many of the industrially produced biotechnological liquids, which comprise enzymes or organic acids, are coloured. The colour of the liquids, e.g. dark brown, occurs naturally in most industrially produced biotechnological liquids due to metabolic mechanisms during the fermentation process. However, many of the products of these processes, for example enzymes, are used for applications, where the product should preferably be colourless or white, such as detergents or as additives for ready-made wheat flour mixes. Thus it is evident that a strong and/or dark colour of a biotechnological liquid decreases considerably the quality and sales value of the liquid. One problem is that the colour forming substances in biotechnological liquids are typically fully soluble which makes their separation from the liquid complicated.

It is known that the colour of a biotechnological liquid or a biotechnical product may be reduced by using chromatographic procedures. These procedures are rather expensive and increase the productions costs of the biotechnological liquid or products.

An object of this invention is to minimise or even totally eliminate the disadvantages existing in the prior art.

Another object of the present invention is also to provide a method with which colour of a biotechnological liquid can be reduced in inexpensive, effective and simple manner.

These objects are obtained with the invention having the characteristics presented below in the characterising parts of the independent claims.

Typical method according to the present invention for reducing colour of a biotechnological liquid, comprises
  obtaining a biotechnological liquid comprising colour forming substances,
  adding and mixing a high-basicity aluminium compound, which has a basicity of at least 50%, to the biotechnological liquid,
  allowing a precipitate and/or flocks comprising colour forming substances to form, and
  separating the precipitate and/or flocks from the biotechnological liquid.

Now it has been surprisingly found out that the colour forming substances are effectively precipitated and/or formed to flocks by addition of an aluminium compound with high basicity to the biotechnological liquid. The formation of flocks and/or precipitate reduces significantly the colour of the liquid phase. The formed flocks and/or precipitate including the colour forming substances can be easily separated from the liquid phase, if required. At the same time the biotechnological liquid retains its other important properties, for example enzyme activity and/or pH value. One of the advantages of the method according to the present invention is its simplicity and inexpensive nature.

In the context of the present application the term "biotechnological liquid" is understood as a liquid or solution which originates from a fermentation process, where organic acids or enzymes are produced. The biotechnological liquid may comprise raw substrates and/or nutrients of the fermentation process, fermentation product(s), microorganisms and possible derivatives, additives added during the fermentation process and gases, such as oxygen and possible other metabolic gas(es) of the fermentation reaction. All these may be present in the biotechnological liquid simultaneously. Biotechnological liquid may be a fermentation broth or a concentrated liquid from a biotechnological process comprising desired products, such as enzymes, organic acids or the like.

According to one embodiment of the present invention the biotechnological liquid is obtained from preparation of different enzymes, such as protease, lipase, cellulose or the like, or from preparation of organic acids, such as citric acid, lactic acid or the like.

The high-basicity aluminium compound, which is used for reducing the colour of the biotechnological liquid, may be polyaluminium chloride, polyaluminium chloride sulphate or any of their mixtures.

According to one advantageous embodiment of the present invention the high-basicity aluminium compound is polyaluminium chloride. Polyaluminium chloride is understood in this application as pre-polymerised aluminium substance, which may be presented also by the general formula $Al_n(OH)_mCl_{(3n-m)}$. It may be produced by the addition of NaOH or $Na_2CO_3$ to $AlCl_3$ or by reacting aluminium hydrate with hydrochloric acid.

The degree of neutralisation, i.e. the replacement of Cl ions with OH ions, may be expressed by using the unit basicity. The basicity of polyaluminium compound may be generally expressed by the following formula $$\% \text{ Basicity} = 100 \times [OH]/3[Al]$$

The higher the basicity, the higher the degree of neutralisation. According to one preferred embodiment of the present invention the aluminium compound is polyaluminum chloride having a basicity of at least 60%, preferably at least 65%, more preferably at least 70%, even more preferably at least 75%, measured by using standard method EN 1302. The basicity of the polyaluminium chloride may be in the range of 50-95% or 60-95%, preferably 65-95%, more preferably 70-90%, even more preferably 75-85%, measured by using standard method EN 1302.

High-basicity polyaluminium chloride is normally used in form of an aqueous solution, which may have aluminium content of 3-15%, preferably 3-14%. Aqueous high-basicity polyaluminium chloride solution may have pH value in the range of 1.5-5, preferably 2.5-4.5.

According to one embodiment of the invention the high-basicity aluminium compound is polyaluminium chloride sulphate. High-basicity polyaluminium chloride sulphate may have basicity in the range of 50-80%, preferably 50-70%. The sulphate content of high-basicity polyaluminium chloride sulphate may be around 2 weight-% of the weight of the dry product.

According to one embodiment of the invention the high-basicity aluminium compound is added in amount of 100-6000 ppm, preferably 300-4000 ppm, more preferably 600-3000 ppm, given as active aluminium.

Preferably the pH of the biotechnological liquid does not significantly change after the addition of the high-basicity aluminium compound. The change in pH value may be less than 1 pH unit, preferably less than 0.5 pH units.

According to one embodiment of the invention a cationic polymer coagulant may also be added to the biotechnological liquid. The cationic polymer coagulant may be used for coagulating fermentation biomass comprising microorganisms and their possible derivatives. The cationic polymer coagulant may be selected, for example, from polydiallyldimethylammonium chloride (poly-DADMAC), a polyamine, such as polyepiamine, or any of their mixtures. Preferably the cationic polymer coagulant is polydiallyldimethylammonium chloride (poly-DADMAC) or polyepiamine. Polydiallyldimethylammonium chloride may have an average molecular weight from 50 000 to 1 000 000, preferably from 100 000 to 500 000. Polyepiamine may have an average molecular weight from 20 000 to 500 000, preferably from 50 000 to 300 000. Use of cationic polymer coagulant in the process together with high-basicity polyaluminium chloride may reduce especially the turbidity of the biotechnological liquid.

According to one embodiment the cationic polymer coagulant may be added to the biotechnological liquid comprising fermentation biomass, whereby at least part of the biomass is allowed to coagulate. The high-basicity aluminium compound is added to the biotechnological liquid, and the precipitate or flocks comprising colour forming substances are allowed to form. The coagulated fermentation biomass and the precipitate and/or flocks comprising colour forming substances are separated in at least one separation step. The cationic polymer coagulant may be added to the biotechnological liquid simultaneously, but separately, with the high-basicity aluminium compound, or the cationic polymer coagulant may be added before or after the addition of the high-basicity aluminium compound. Preferably the cationic polymer coagulant is added before the addition of the high-basicity aluminium compound or simultaneously with the high-basicity aluminium compound. The addition of cationic polymer coagulant and the high-basicity aluminium compound may be done to the biotechnological liquid comprising fermentation product(s) as well as microorganisms and their possible derivatives According to one embodiment of the invention the high-basicity aluminium compound is added to the biotechnological liquid after the separation of the biomass, i.e. microorganisms and their possible derivatives, from the biotechnological liquid.

According to one preferred embodiment the high-basicity aluminium compound is added to the biotechnological liquid after the separation of the microorganisms and their possible derivatives from the biotechnological liquid, and after one or several concentration steps, where the biotechnological liquid comprising the biotechnological product, such as enzyme or organic acid is concentrated. According to one advantageous embodiment the high-basicity polyaluminium chloride is added to the concentrated biotechnological liquid and the formed flocks and/or precipitate of colour forming substances are separated in at least one solid-liquid separation step.

The formed precipitate or formed flocks of the colour forming substances may be separated from the liquid phase by filtration, microfiltration and/or centrifugation. The separation may be performed in at least one separation step, which includes one or more of the following: a belt filter, vacuum filter, pressure filter or microfiltration membrane.

According to one embodiment of the invention it is possible to add an additional flocculant, such as anionic polyacrylamide, to the biotechnical liquid after the addition of the high-basicity aluminium compound. The additional flocculant improves the separation of the precipitate and/or flocks comprising colour forming substances e.g. by filtration.

Some embodiments of the invention will be described in more detail with reference to appended schematic drawing.

FIG. 1 shows schematically a flow chart of a fermentation process for enzyme production, where the method according to the invention may be employed. Microorganisms and nutrients are fed to a fermentation tank 1, where the fermentation process is carried out. Biotechnological liquid is transferred to a harvest tank 2 and further to solid-liquid separation stage 3. After solid-liquid separation stage 3 the biotechnological liquid is concentrated in a concentration stage 4, comprising at least one concentration step, e.g. ultrafiltration. A permeate flow 5 is discharged from the process and concentrated biotechnological liquid is transferred to further processing stage 6, which can comprise e.g. spray drying of the liquid in order to obtain a solid enzyme product 7. Possible places for addition of a high-basicity aluminium compound are indicated with arrows A. It is possible to add high-basicity aluminium compound after the harvest tank 2 and before the solid-liquid separation step 3. In that case the precipitated or flocked colour forming substances are separated from the biotechnological liquid comprising the desired product at the solid-liquid separation stage 3. Alternatively the high-basicity aluminium compound may be added after the concentration step 4 of the biotechnological liquid. In that case the further processing stage 6 comprises also a suitable separation step for separation of the precipitated or flocked colour forming substances.

EXPERIMENTAL

Some embodiments are presented in the following non-limiting examples.

EXAMPLE 1

In Example 1 a fermentation broth from enzyme production, having total solids of 12 weight-%, is treated with a high-basicity aluminium compound and a cationic polymer coagulant at room temperature at pH 6. The used cationic polymer coagulant is polydiallyldimethylammonium chloride and the high-basicity aluminium compound is polyaluminium chloride having basicity of about 83%. Cationic polymer coagulant is added in amount of 10 kg/(ton dry solids).

The removal of the coloured substances is done at the same time with dewatering of the broth. The cationic polymer coagulant and the high-basicity aluminium compound are added into the fermentation broth successively. The dosing is done to 200 ml of broth in the order 1) cationic polymer coagulant and 2) aluminium compound. The cationic polymer coagulant is added upon fast mixing followed by a short slow mixing period of 1 minute. High-basicity aluminium compound is then added upon fast mixing followed by a short slow mixing period of 5 minutes. The samples are allowed to sediment for 1 hour before centrifugation. The flocks are separated from the supernatant by centrifugation, 3000 rcf (rcf=relative centrifugal force) for 10 minutes.

The colour intensity is measured by spectrophotometer (HACH DR2800) from samples diluted in ratio 1/30 at 455 nm wavelength. The colour is expressed in mg/l platinum as chloroplatinate ion (Pt—Co). Results are shown in Table 1.

TABLE 1

Colour removal results for Example 1.

| Aluminium compound, ($Al^{3+}$ ppm (mg/l)) | Residual colour (mg/l Pt (Pt—Co)) |
|---|---|
| 0 | 152 |
| 500 | 135 |
| 1000 | 118 |
| 2000 | 104 |
| 3000 | 95 |

The colour intensity of the fermentation broth treated only with cationic polymer coagulant and without addition of the high-basicity aluminium compound was taken as an original colour level of the fermentation broth. The residual colour intensity decreases to the level of about 60% by treating the sample with the high-basicity aluminium compound.

EXAMPLE 2

In Example 2 Samples A and B of concentrated enzyme liquid, having total solids about 10 weight-%, are treated with a high-basicity aluminium compound and a medium-basicity aluminium compound at room temperature at pH 6. The used the high-basicity aluminium compound is a polyaluminium chloride having basicity of about 83% used for treating Sample A. A second polyaluminium chloride is a medium-basicity aluminium compound having basicity of about 42% is used for treating the Reference Sample B.

The high-basicity aluminium compound is added to 100 ml of enzyme liquid of Sample A upon fast mixing of 10 seconds, followed by a slow mixing period of 10 minutes. The Sample A is allowed to sediment for 30 min before centrifugation. The flocs are separated from the supernatant by centrifugation, 3000 rcf (rcf=relative centrifugal force) for 10 minutes.

The Reference Sample B is treated in corresponding manner but using the medium-basicity polyaluminium compound The colour intensity for Samples A and B are measured by spectrophotometer (HACH DR2800) from samples diluted in ratio 1/30 at 455 nm wavelength. The colour is expressed in mg/l platinum as chloroplatinate ion (Pt—Co). Results are shown in Table 2.

TABLE 2

Colour removal results for Example 2.

| Aluminium compound kg $Al^{3+}$/t DS | Sample A Residual colour (mg/l Pt (Pt—Co)) | Reference Sample B Residual colour (mg/l Pt (Pt—Co)) |
|---|---|---|
| 0 | 459 | 459 |
| 500 |  | 320 |
| 1000 | 250 | 192 |
| 1500 | 211 | 218 |
| 2000 | 165 | 291 |
| 2500 | 138 | 355 |

As can be seen in Table 2 the colour reduction capacity of the high basicity aluminium compound with basicity about 83% is remarkably better in comparison to the medium-basicity aluminium compound with basicity about 42%

Even if the invention is described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for reducing colour of a biotechnological liquid obtained from enzyme preparation or from preparation of organic acids, comprising the steps of:
   obtaining a biotechnological liquid from a fermentation process comprising enzymes or organic acids and colour forming substances,
   adding and mixing a high-basicity aluminium compound being polyaluminium chloride or polyaluminium chloride sulphate or a mixture thereof, which has a basicity content in a range of 75-85%, to the biotechnological liquid,
   allowing precipitate and/or flocks comprising the colour forming substances to form, and
   separating the precipitate and/or flocks from the biotechnological liquid,
   wherein after separation of the precipitate and/or flocks from the biotechnological fluid, the biotechnological fluid comprises the produced enzymes or organic acids.

2. The method according to claim 1, wherein the aluminium compound is a mixture of polyaluminum chloride and polyaluminium chloride sulphate.

3. The method according to claim 1, wherein the aluminium compound is polyaluminium chloride and it is used in form of an aqueous solution, which has aluminium content of 3-15% or 3-14%.

4. The method according to claim 1, having a step of adding the aluminium compound to the biotechnological liquid after separation of biomass from the biotechnological liquid.

5. The method according to claim 1, having additional steps of:
   adding a cationic polymer coagulant to the biotechnological liquid comprising biomass and allowing at least part of the biomass to coagulate,
   adding the aluminium compound to the biotechnological liquid, and allowing the precipitate and/or flocks comprising colour forming substances to form, and
   separating the coagulated biomass as well as the precipitate and/or flocks in at least one separation step.

6. The method according to claim 5, wherein the cationic polymer coagulant is polydiallyldimethylammonium chloride (poly-DADMAC), a polyamine or any of their mixtures.

7. The method according to claim 1, wherein the aluminium compound is added in amount of 100-6000 ppm 300-4000 ppm, or 600-3000 ppm.

8. The method according to claim 1, wherein the precipitate and/or flocks comprising colour forming substances are separated by filtration, microfiltration and/or centrifugation.

* * * * *